United States Patent
De Sousa Dias et al.

(10) Patent No.: US 10,087,162 B2
(45) Date of Patent: Oct. 2, 2018

(54) PREPARATION OF DIALKYL ESTERS OF 2,5-FURANDICARBOXYLIC ACID

(71) Applicant: Synvina C.V., Amsterdam (NL)

(72) Inventors: Ana Sofia Vagueiro De Sousa Dias, Amsterdam (NL); Benjamin McKay, Amsterdam (NL); Victor Peter Charles Vreeken, Amsterdam (NL); Gerardus Johannes Maria Gruter, Amsterdam (NL); Johannes Maria Franciscus Sijben, Amsterdam (NL)

(73) Assignee: Synvina C.V., Amsterdam (NL)

( * ) Notice: Subject to any disclaimer, the term of this patent is extended or adjusted under 35 U.S.C. 154(b) by 0 days.

(21) Appl. No.: 15/525,426

(22) PCT Filed: Nov. 10, 2015

(86) PCT No.: PCT/NL2015/050781
§ 371 (c)(1),
(2) Date: May 9, 2017

(87) PCT Pub. No.: WO2016/076711
PCT Pub. Date: May 19, 2016

(65) Prior Publication Data
US 2017/0320845 A1    Nov. 9, 2017

(30) Foreign Application Priority Data
Nov. 10, 2014 (NL) ................................. 2013765

(51) Int. Cl.
C07D 307/02 (2006.01)
C07D 307/68 (2006.01)

(52) U.S. Cl.
CPC ........ C07D 307/68 (2013.01); *C07B 2200/13* (2013.01)

(58) Field of Classification Search
CPC .......................... C07D 307/68; C07B 2200/13
USPC ........................................................ 549/485
See application file for complete search history.

(56) References Cited

U.S. PATENT DOCUMENTS

| | | | |
|---|---|---|---|
| 4,160,692 A | 7/1979 | Mitchell et al. | |
| 5,679,312 A | 10/1997 | Jin et al. | |
| 8,519,167 B2 | 8/2013 | Munoz De Diego et al. | |
| 8,658,810 B2 | 2/2014 | Partin et al. | |
| 2012/0302768 A1 | 11/2012 | Janka et al. | |
| 2013/0345447 A1* | 12/2013 | Shaikh | C07D 307/68 549/485 |
| 2013/0345448 A1* | 12/2013 | Shaikh | C07D 307/46 549/485 |

FOREIGN PATENT DOCUMENTS

| | | |
|---|---|---|
| WO | 2011/043661 A1 | 4/2011 |
| WO | 2013/191940 A1 | 12/2013 |
| WO | 2013/191942 A1 | 12/2013 |

OTHER PUBLICATIONS

Hewitt, Geoffrey F., Evaporators, DOI:10.1615/A to Z.e. evaporators, Feb. 2011, p. 1-7 (Year: 2011).*

* cited by examiner

*Primary Examiner* — Taylor V Oh
(74) *Attorney, Agent, or Firm* — Hoffmann & Baron, LLP

(57) ABSTRACT

Dialkyil esters of 2,5-furandicarboxylic acid are prepared in a process including: contacting an acid starting composition having 2,5-furandicarboxylic acid with an excess of alkanol to form an esterification product having the dialkyil ester of 2,5-furan dicarboxylic acid, water and unreacted alkanol; separating at least part of the unreacted alkanol and water from the esterification product to yield a solid crude product composition having the dialkyil ester of 2,5-furandicarboxylic acid; and subjecting at least part of the solid crude product composition to an evaporation step, where the dialkyl ester of 2,5-furandicarboxylic acid is evaporated and subsequently condensed to yield purified dialkyil ester of 2,5-furandicarboxylic acid.

14 Claims, No Drawings

PREPARATION OF DIALKYL ESTERS OF 2,5-FURANDICARBOXYLIC ACID

CROSS-REFERENCE TO RELATED APPLICATIONS

This application is the National Stage of International Application No. PCT/NL2015/050781 filed Nov. 10, 2015, which claims the benefit of Netherlands Application No. NL 2013765, filed Nov. 10, 2014, the contents of which is incorporated by reference herein.

FIELD OF THE INVENTION

The present invention relates to a process for the preparation of dialkyl esters of 2,5-furandicarboxylic acid. More in particular it relates to the preparation of compositions comprising such esters having a low color.

BACKGROUND OF THE INVENTION 2,5-Furandicarboxylic acid ("FDCA") is a dicarboxylic acid for which the commercial interest has grown recently. The diacid or its diester has been found to be particularly interesting for the preparation of poly(alkylene-2,5-furandicarboxylate), in which preparation FDCA is condensed with an alkylene glycol, such as monoethylene glycol (MEG). The polymer obtained from the polymerization of FDCA or its diester and MEG, polyethylene-2,5-furandicarboxylate (PEF), can be used as alternative for polyethylene terephthalate (PET) or, due to its properties, can be used in areas where PET cannot be used. As one of the advantages of using FDCA it is considered that FDCA is obtainable from sustainable sources. In WO 2011/043661 and U.S. Pat. No. 8,519,167 methods are described wherein 5-hydroxymethyl furfural and derivatives thereof are converted into FDCA and esters thereof. As explained in these patent documents, the starting material 5-hydroxymethylfurfural and derivatives thereof can be obtained from carbohydrate-containing sources, such as fructose, glucose, sucrose, starch, cellulose etc.

US 2012/0302768 discloses that the oxidation process of 5-hydroxymethylfurfural and derivatives thereof leads to the formation of a mixture of 2,5-furan-dicarboxylic acid, 2-formyl-furan-5-carboxylic acid and, optionally, some other furan derivatives, such as alkyl esters of 2-formyl-furan-5-carboxylic acid. Although it is stated that purified 2,5-furandicarboxylic acid can be obtained by washing, it was found that also the purified product still contained an amount of 2-formyl-furan-5-carboxylic acid. It is acknowledged in US 2012/0302768 that significant concentrations of mono-functional molecules like 2-formyl-furan-5-carboxylic acid in the 2,5-furan-dicarboxylic acid product are particularly detrimental to polymerization processes as they may act as chain terminators during a polyester condensation reaction.

It has been found that washing does not yield pure product. It is believed that 2-formyl-furan-5-carboxylic acid is included in the crystals of 2,5-furan-dicarboxylic acid whereby the purification by washing becomes unfeasible. Purification of the corresponding ester products was found to be easier.

Many prior art documents wherein the preparation of poly(alkylene-2,5-furan dicarboxylate) is described, mention that the resulting polymers are colored. In order to be able to compete with transparent PET it is desirable that poly(alkylene-2,5-furandicarboxylate) and thus the starting materials in the preparation thereof are as colorless as possible.

The need for a method for the purification of esterification products of FDCA has been acknowledged in WO 2013/191942. In order to meet this need WO 2013/191942 describes a process wherein an FDCA-containing composition is reacted with an alcohol component, and a portion of the alcohol component is separated from the product of the esterification reaction to obtain an ester composition comprising the dialkyl ester of FDCA as solid material. The ester composition is subsequently purified. The purification of the ester composition comprises solids separation, washing, crystallization, solid-liquid separation, re-dissolution and recrystallization. WO 2013/191942 states that in this way an ester composition can be obtained that contains at least 96% wt of solid dialkyl ester of FDCA and less than 3% wt of the monoalkyl ester of FDCA, less than 3% wt of alkyl-5-formyl-2-furancarboxylate, and less than 1% wt of FDCA and that shows a color component b* of at most 5.

Applicants have found that the mere crystallization of esterified FDCA does not result in a satisfactory removal of compounds that are colored or are precursors of color-producing compounds. By repeating the recrystallization steps it may be possible to obtain a certain level of purity. However, such repetitions will inevitably also result in a low eventual yield, since together with impurities also desired dialkyl ester product will remain in the mother liquor from which the recrystallizations are being carried out. Hence, there is a need for a process for the preparation of dialkyl esters of FDCA, wherein the yield of pure dialkyl ester is improved by avoiding the loss due to one or more recrystallization steps.

SUMMARY OF THE INVENTION

Accordingly, the present invention provides a process for the preparation of the dialkyl esters of 2,5-furandicarboxylic acid which process comprises
  contacting an acid starting composition comprising 2,5-furandicarboxylic acid with an excess of alkanol to form an esterification product comprising the dialkyl ester of 2,5-furan dicarboxylic acid, water and unreacted alkanol;
  separating at least part of the unreacted alkanol and water from the esterification product to yield a solid crude product composition comprising the dialkyl ester of 2,5-furandicarboxylic acid; and
  subjecting at least part of the solid crude product composition to an evaporation step, wherein the dialkyl ester of 2,5-furandicarboxylic acid is evaporated and subsequently condensed to yield purified dialkyl ester of 2,5-furandicarboxylic acid.

DETAILED DESCRIPTION OF THE INVENTION

It has surprisingly been found that evaporation of the dialkyl ester of FDCA from the crude product composition leaves the main compounds that cause coloration in the residue. In addition, any impurities that may cause chain termination in a polycondensation, such as 5-formyl-2-furancarboxylic acid and alkyl esters thereof, are also contained in the residue. The application of this purification method not only results in a very pure dialkyl ester product but it also yields minimal losses of dialkyl ester product.

In this context it is observed that in U.S. Pat. No. 8,658,810 a process for the preparation of the dialkyl ester of FDCA is described, wherein an esterification product is obtained from the reaction of FDCA with an alcohol. The alcohol is separated from the esterification product by means of flash evaporation. The flash evaporation yields an alcohol-rich vapor and a liquid composition that comprises the dialkyl ester of FDCA. The dialkyl ester of FDCA is separated from the esterification product by means of a series of distillation columns. In a first distillation any further alcohol is separated from the esterification product. Then other by-product esters are separated by distillation to yield a residue that comprises the monoalkyl ester and the dialkyl ester of FDCA. In a further distillation the separation between the monoalkyl ester and the dialkyl ester is carried out.

It is evident that this purification route is quite different from the evaporation step applied in the present process.

Evaporation takes place at the surface and may be carried out at a temperature below the boiling point of the dialkyl ester of FDCA. This represents a considerable saving on heating energy. Evaporation is especially suitable for the esterification product containing high-boiling compounds such as the dialkyl ester of FDCA. Distillation requires that the esterification product is brought to the boiling temperature, which tends to prolong the residence time in the distillation column. Evaporation allows very short residence times. As indicated above, the present process including an evaporation step is particularly advantageous as the compounds that cause coloration of the resulting dialkyl ester of FDCA are effectively separated from the dialkyl ester by means of such an evaporation step. During the prolonged residence time in a distillation column the esters run the risk for thermal degradation or further reactions. One of the potential reactions is the formation of polycyclic furan compounds. Especially when these compounds are conjugated unsaturated compounds, they tend to cause coloration. Hence, rather than removing impurities and coloration causing compounds, distillation may increase the risk that coloration compounds are formed. By evaporation and the short residence times associated with evaporation the risk of forming coloration causing compounds is reduced.

Evaporation is basically a separation step which uses heat transfer to separate products presenting differences at boiling point and wherein compounds evaporate from the surface. Since evaporation is a surface-related phenomenon evaporation is often applied to liquid films. There are many commercial type of equipment for evaporation. Such equipment includes stirrer evaporators, rising film evaporators wherein a pump moves boiling feed up along tubes, circulation evaporators which are similar to rising film evaporators, but wherein liquid that is recovered at the top is recycled to the bottom of the evaporator; falling film evaporators, wherein both vapor and liquid move downwards, usually along heat exchanger tubes or heat exchanger plate and wiped film evaporators wherein wiper blades provide a thin film of liquid on the inside of a vessel. Also equipment that is usual for laboratories, such as rotary evaporators or centrifugal evaporators, may be used.

The evaporation is suitably carried out at temperatures in the range of 120 to 250° C., more preferably, in the range of 130 to 200° C. The lower limit should be such that the solid crude product composition is molten. The upper limit may be selected such that the vapor pressure of the dialkyl ester of FDCA is sufficiently high to allow for an efficient separation. The upper temperature limit is preferably relatively low, to reduce the risk that the dialkyl ester of FDCA or any other compound thermally degrades. Therefore, the temperature is preferably from 130 to 180° C. To provide for a sufficiently large difference in separation between the dialkyl ester of FDCA and the monoester and other impurities, the evaporation is suitably conducted at reduced pressure, preferably below 100 mbar. A suitable pressure is in the range of 3 to 50 mbar.

The crude product composition is fed into an evaporator is a feed rate that can suitably be selected by the skilled person. Depending on the feed rate the residence time of the composition in the evaporator is determined. This may also have an effect on the division of the composition in a vapor fraction and a residue fraction. Depending on the purity of the product composition, the vapor fraction may be enhanced; the purer the crude product composition is, the larger the vapor fraction may be. Typically the split between vapor and residue will be in the range of 15-95% wt vapor and 85-5% wt residue, based on the weight of the product composition. For relatively pure product compositions, i.e. when the product composition contains at most 2000 ppm of impurities, the split between vapor and residue may be in the range of 80-95% wt vapor and 20-5% wt residue.

One of the advantages of evaporation resides in the short residence time. Dependent on the equipment and the product composition the residence time of the product composition in the evaporator can be determined by the skilled person. Suitably, the residence time is very short and may typically be in the range of 5 sec to 40 min, preferably from 0.1 to 30 min, more preferably from 0.25 to 20 min. The actual contact time of the product composition with the heated surface in an evaporator may be in the order of seconds, so that volatile dialkyl ester vaporizes. The vapor is then withdrawn from the evaporator. The residue containing the majority, if not all, of the impurities is quickly discharged.

A preferred evaporator for use in the present invention is a wiped film evaporator. The wiped film evaporators (also referred to as agitated thin-film evaporators) preferred for use in the distillation process of the present invention are known in the art and are available commercially. Typically, wiped film evaporators comprise a cylindrical evaporating vessel. The vessel may be either vertical or horizontal, with vertically arranged vessels being preferred. The evaporator further comprises a rotor mounted within the cylindrical evaporating vessel and provided with a number of wiper blades or wiper rollers, and a motor is provided to drive the rotor. The rotor is arranged within the cylindrical evaporating vessel so that, upon rotation by the motor, the wiper blades or rollers are caused to move over the inner surface of the cylindrical vessel. The wiper blades or rollers may contact the inner surface of the cylindrical vessel or, alternatively, a small gap or clearance may be left between the tips of the wiper blades or rollers and the inner surface of the cylindrical vessel.

In operation, the portion of the solid crude dialkyl ester of FDCA mixture to be separated is supplied to the evaporator to form a thin film over the inner surface of the cylindrical vessel. The film is heated, typically by means of indirect heat exchange with a heating medium such as steam or superheated steam. The action of the wiper blades or rollers results in turbulence in the film, which in turn improves heat and mass transfer. In addition, the wiper blades or rollers ascertain an even distribution of the composition over the inner surface of the vessel. Under the action of the wiper blades or rollers and the heating, the lighter components of the mixture are caused to evaporate and the heavier components, such as the monoalkyl ester and the coloration-causing compounds or precursors thereof remain in the liquid phase. The wiped film evaporator is suitably operated under vacuum. An example of a wiped film evaporator is disclosed in U.S. Pat. No. 4,160,692.

The present process is especially advantageous when the acid starting material comprises 2,5-furandicarboxylic acid and the monoalkyl ester thereof. In such a case also the monoalkyl ester is at least partially converted to the desired dialkyl ester in the esterification reaction. Amounts of 10 to 90% wt of the monoalkyl ester, based on the weight of the monoalkyl ester and FDCA can suitably be used. The mixture of the monoalkyl ester of FDCA and FDCA is included in the acid starting material that is contacted with the alkanol. Preferably, at least some of the compounds in the acid starting material are liquid. That does not mean that all components of the acid starting material must be liquid. In view of the high melting temperature of FDCA itself, the acid starting material typically comprises a slurry of solid FDCA and liquid monoalkyl ester of FDCA.

In the process according to the present invention the evaporation step can be repeated one or more times. It has been found that evaporation can effectively be used to remove coloration causing compounds from the solid crude product compositions. This can even effectively be done when the product composition contains a significant amount of impurities. The residue of any evaporation may be subjected to a further evaporation step, thereby yielding a further distillate. The further distillate thus obtained may be very pure already and thus can be used as obtained. If the further distillate contains any amount of impurities that is found too high, it may again be subjected to evaporation to yield a purer distillate. In this way the impurities can be concentrated in the eventual residue, whereas the yield of pure dialkyl ester of FDCA is optimized in the distillates of the subsequent evaporation steps.

Compounds that are contained in the acid starting material that comprises FDCA and the monoalkyl ester thereof can easily be obtained from the process that has been described in the above-mentioned U.S. Pat. No. 8,519,167 and WO 2011/043661. In these documents the preparation of FDCA and esters thereof has been described by means of the oxidation of 5-hydroxymethyl furfural and derivatives thereof with an oxygen-containing gas. The reaction is suitably conducted over a catalyst system that comprises cobalt and manganese, and suitably also comprises bromine. Accordingly, the acid starting material preferably comprises the oxidation product of a compound selected from 5-hydroxymethylfurfural, an ether thereof, an ester thereof and mixtures of any such compounds, with an oxygen-containing gas. In particular, the acid starting material is the oxidation product of an ether of 5-hydroxymethyl furfural. The ether is preferably the methyl or ethyl ether, more in particular the methyl ether. The oxidation of these ethers results in a mixture of FDCA and the monomethyl or monoethyl ester, respectively. Such has been described in the above-mentioned U.S. Pat. No. 8,519,167.

It is advantageous if the boiling point of the alkanol, i.e. a mono-alcohol, used in the present process is not too high. The separation of the unreacted alkanol and water from the esterification product is advantageously conducted by means of distillation, flash distillation or evaporation. Thereto, it would be advantageous if the boiling point of the alkanol is not too high. Suitably, the boiling point is sufficiently low to enable an easy separation between the low-boiling alkanols and the dialkyl ester product with significantly higher boiling points. Since the alkanols having 1 to 4 carbon atoms have atmospheric boiling points below 120° C., which is significantly lower than the boiling point of the corresponding dialkyl esters of these alkanols with FDCA, the alkanol preferably comprises 1 to 4 carbon atoms. In this way the boiling points between the alkanols and water on the one hand and the boiling point of the mono- and diester of FDCA on the other hand are sufficiently different to facilitate the separation. Since methanol does not form an azeotrope with water, the separation of water and methanol is fairly simple and, thus, the use of methanol is especially advantageous.

The amount of alkanol relative to the amount of FDCA and monoalkyl ester, if present, is not critical. A stoichiometric excess is applied in order to shift the equilibrium of the esterification reactions towards the esters. The molar ratio of alcohol to FDCA is therefore more than 2:1, on a mole/mole basis.

The esterification reaction is auto-catalyzed; the acid function of FDCA provides for catalytic activity. Therefore, FDCA and the alkanol are preferably contacted in the substantial absence of an esterification catalyst. Hence the addition of strong mineral acids, such as sulphuric acid, to catalyze the esterification reaction is not needed. However, when the esterification product is obtained in a continuous process wherein the alkanol is continuously contacted with the acid composition it may be advantageous to have an acidic catalyst present. The acidic catalyst is preferably a solid catalyst. Such solid catalysts are preferably selected from the group consisting of acidic zeolites, ion exchange resins and mixtures thereof. The provision of such solid catalysts may be suitable when the process according to the present invention is carried out in a trickle-bed reactor, a slurry reactor, a slurry bubble column, a reactive stripping columns or a monolith reactor.

These reactors provide esterification zones wherein the contact of the acid composition and the alkanol takes place and are preferably thus, that they enable the continuous removal of alkanol from the esterification zone. The esterification process conditions are known to the skilled person. They typically include that the contact of FDCA with the excess of alkanol is conducted at a temperature of 150 to 300° C., preferably from 160 to 260° C., and at a pressure of 5 to 25 bar. The contact time of the contact of FDCA and the excess alkanol is suitably in the range of 0.1 to 3 hr, preferably from 0.3 to 1.5 hr.

A specifically preferred reactor is a reactive stripping column. In such a reactor the acid starting composition and the alkanol are contacted counter-currently, wherein the alkanol is provided as a vapor. A vapor of alkanol and water, formed during the esterification reaction, is withdrawn from the upper part of the reactive stripping column, and a liquid phase comprising the esterification product is discharged at the lower part of the reactive stripping column. To reduce back-mixing the column is suitably provided with internals, such as sieve plates and/or a packing. An example of a reactive stripping column is disclosed in U.S. Pat. No. 5,679,312. If the present process is carried out in a reactive stripping column the separation of unreacted alkanol and water from the esterification product takes place continuously in the reactive stripping column.

When the process according to the present invention employs an acid starting composition comprising FDCA and a monoester thereof, it gives the opportunity to obtain purified product. It has been found that it is difficult to separate FDCA and the monoester thereof from by-products of the oxidation by distillation or crystallization. One such by-product is 5-formyl-2-furancarboxylic acid, in addition to coloration-causing compounds and precursors thereof. Since the process according to the present invention enables the skilled person to esterify virtually any acid into its ester and since the esters are more easily separable from each other than their corresponding acids, this process gives the skilled person a tool to obtain purified FDCA in the form of its dialkyl ester.

After the separation of the unreacted alkanol from the esterification product a solid crude product composition comprising the dialkyl ester of FDCA is obtained. This solid crude product composition comprises the dialkyl ester of FDCA in a major amount, but typically it may also contain minor amounts of the monoester of FDCA and alkyl 5-formyl-2-furancarboxylate. Therefore, the crude dialkyl ester of FDCA is suitably pre-purified in a concentration zone before it is subjected to the purification step or steps. The pre-purification may be conducted in a way similar to the first purification steps of WO 2013/191942. That means that the solid crude product composition is suitably subjected to one or more of the treatments selected from washing with a liquid washing composition and crystallization. In addition, re-crystallization and/or melt crystallization may be applied. The pre-purification may comprise one or more of these treatments, and each treatment may be done once or repeated one or more times. In a preferred embodiment the solid crude dialkyl ester of 2,5-furandicarboxylic acid is washed in a washing zone to yield washed composition, and the washed composition is crystallized in a crystallization zone to yield crystallized composition that is being subjected to the evaporation step. In this way by-products, such as alkyl 5-formyl-2-furancarboxylate, are effectively and cheaply separated from the solid crude product composition.

The opportunity to subject the solid crude product composition to a pre-purification represents a considerable advantage over the process according to U.S. Pat. No. 8,658,810. Whereas in the process according to the present invention at least apart of by-products can be removed via a relatively simple and cheap manner as washing and/or crystallization, the liquid esterification product obtained in the process according to U.S. Pat. No. 8,658,810 has to be subjected to a sequence of expensive and energy-consuming distillation steps. It is evident that the process according to the present invention is more efficient that the process according to U.S. Pat. No. 8,658,810.

Subsequently, the composition obtained after the pre-purification is fed to the evaporation step. The dialkyl ester of FDCA is removed from the evaporator as a vapor and is subsequently condensed, to yield purified dialkyl ester product.

Alternatively, or when it is desired to separate by-products such as alkyl 5-formyl-2-furancarboxylate from the eventual purified dialkyl ester of FDCA, the treatments that are described hereinabove for the pre-purification, may be applied after the evaporation step. In such an embodiment, the solid crude product composition is subjected to the evaporation step, so that may heavy compounds, such as the monoalkyl ester of FDCA and coloration-causing compounds or precursors thereof are discharged as a liquid stream, and the dialkyl ester, together with some other relatively light ester products, such as alkyl 5-formyl-2-furancarboxylate, are removed as vapor. The thus obtained dialkyl ester product is condensed. The thus purified dialkyl ester may be contaminated with a minor amount of alkyl 5-formyl-2-furancarboxylate. Via re-crystallization alkyl 5-formyl-2-furancarboxylate can very effectively be separated from the purified dialkyl ester of FDCA.

As to the treatments above, both for the pre-purification and the purification after the evaporation step, the skilled person will understand how the washing, crystallization, re-crystallization and melt crystallization can be carried out. Suitable washing liquids may include water, alcohol, or water and alcohol mixtures, although the liquid is not limited to the use of alcohols. Crystallization and re-crystallization may be carried out from a solvent such as an alcohol or an alcohol/water mixture. The crystallization may for instance be performed by evaporative cooling. Melt crystallization may be conducted in the appropriate equipment at a temperature around the melting temperature of the composition to be treated.

Although the process according to the present invention may be carried out in a batch or semi-batch mode, it is preferred to conduct this process as a continuous process.

The present invention enables the obtaining of very pure and very transparent dialkyl esters of FDCA. Accordingly, the present invention also provides an ester composition comprising dialkyl ester of 2,5-furandicarboxylic acid wherein the composition comprises 99 to 99.9% wt of dialkyl ester of 2,5-furandicarboxylic acid, 1 to 0.1% wt of monoalkyl ester of 2,5-furandicarboxylic acid, the percentages based on the weight of the composition, and which composition has a color of at most 0.005, as measured by absorbance of a 30 mg/L solution in DMSO at a wavelength of 400 nm. Although the specification of U.S. Pat. No. 8,658,810 describes the desired purity of ester composition that allegedly results in the process described therein, no examples or other proof is provided that such purity can be actually attained by the process. The very pure and very transparent ester composition mentioned above is therefore considered novel.

The dialkyl ester product obtained from the process according to the present invention may be used as such, e.g. in the preparation of a polyester such as a poly(alkylene-2,5-furandicarboxylate). It is also possible to use the purified dialkyl ester product to yield pure FDCA itself. For that purpose the dialkyl ester of FDCA is suitably hydrolyzed to the alkanol and FDCA. Therefore the dialkyl ester product is advantageously contacted with water for hydrolysis or saponification, to obtain a product composition, comprising FDCA.

By saponification is understood the reaction of an ester with a base whereby an alcohol and salt of the acid is formed. The process usually involves the reaction of an aqueous alkali metal base, such as NaOH or KOH, with an ester to form an alkali metal salt. The alkali metal base is usually present in at least a stoichiometric amount to allow for the formation of the salt. Acidification of the salt results in the production of FDCA as the acid.

Hydrolysis of esters is well known in the art. The reaction comprises contacting the ester in question with water. Suitably, the water has been acidified or rendered alkaline. Acids and bases tend to catalyse the hydrolysis of the ester. Therefore, the purified dialkyl ester of FDCA is suitably contacted with water in the presence of a hydrolysis catalyst. The catalyst can be selected from a wide range of acid or alkaline compounds. It is most convenient to apply inorganic acids, such as sulphuric acid, hydrochloric acid, nitric acid and the like. Also the use of Lewis acids, such as aluminium trichloride, may be used. Suitable alkaline catalysts include the alkali metal hydroxides, such as sodium or potassium hydroxide, but salts of weak organic acids may also be used. Salts of formic acid, acetic acid, propionic acid or butyric acid are suitable examples. The cation can be any metal ion, such as an alkali metal ion or alkaline earth metal ion. Other metal salts of such weak organic acids, such as the zinc salts, may also be used. It is advantageous if the salts are soluble in water. The skilled person will realize that the nature of the hydrolysis catalyst is not of critical importance.

Although the hydrolysis catalyst may increase the reaction rate of the hydrolysis it may have the drawback that by introducing the catalyst an extraneous compound is added that may contaminate the resulting acids. Therefore, the hydrolysis of the purified dialkyl ester of FDCA, i.e. the contact of the purified dialkyl ester with water, is suitably carried out in the absence of a hydrolysis catalyst. It has appeared that the conversion of the esters in the purified dialkyl ester of FDCA is running smoothly also without an additional hydrolysis catalyst. Once the hydrolysis starts and FDCA and the monoester of FDCA are formed, the acidic functions of these compounds auto-catalyze the hydrolysis further. Since the risk of contamination is being avoided by carrying out the hydrolysis in the absence of an additional hydrolysis catalyst, such a process is preferred.

Hydrolysis conditions are well known in the art. It is conventional to heat the ester in water in the presence or absence of an acid or a base. A suitable temperature range may be from 100 to 200° C. Since in the present case it has been found that it is advantageous to conduct the hydrolysis at temperatures above 100° C., it is desirable to apply a pressure above 1 bar. Therefore, the purified dialkyl ester of FDCA is preferably contacted with water at a temperature of 120 to 180° C. and a pressure of 5 to 30 bar.

Saponification conditions may be the same as those of the hydrolysis. However, the temperature may even be lower, e.g. as low as 60° C. The hydrolysis temperature ranges suitably from 60 to 200° C. The pressure may range from about 1 to 30 bar.

The process will be further illustrated by means of the following Example.

EXAMPLE 1

In a wiped film evaporator a solid crude product composition comprising dimethyl ester and the monomethyl ester of FDCA was subjected to evaporation. The composition contained about 1% wt of the monomethyl ester of FDCA and about 200 ppm of other impurities. The balance was dimethyl-2,5-furandicarboxylate. The wiped film evaporator was operated at different feed rates to obtain different ratios of vapor and residue fractions. The total duration of each test lasted 5 minutes. The evaporator was operated at a pressure of about 10 mbar and at a temperature of about 157° C. The temperature of the solid crude product composition that was fed into the evaporator was 150±2° C. The hot product composition was divided in a distillate vapor and a residue. The vapor was recovered at a temperature of 141-142° C., whereas the residue was discharged from the wiped film evaporator at a temperature of 139° C. The vapor was condensed to yield purified dimethyl-2,5-furandicarboxylate in a condenser located downstream of the evaporator and operating at a temperature of 120° C.

The vapors and the residues were analyzed. Amongst the impurities traces of FDCA and polycyclic furan compounds were identified.

The analytical results of the composition of the vapors and the residues are shown in Table 1 below. The Table shows the Experiment No., the feed rate of the composition in the evaporator (F), the fraction of the vapor (V) and residue (R), respectively, based on the solid crude product composition, and the content of the dimethyl ester of FDCA, (FDCA-DME), the monomethyl ester of FDCA (FDCA-ME), and the impurities in the resulting vapor and residue. The percentages are based on the vapor and residue fractions, respectively.

TABLE 1

| Exp. | F, kg/h. | V/R | Fraction, % wt | FDCA-DME, % wt | FDCA-ME, % wt | Impurities, % wt |
|---|---|---|---|---|---|---|
| 1 | 6.8 | V | 84.5 | 99.5 | 0.5 | — |
| 1 | 6.8 | R | 15.5 | 96.1 | 3.8 | 0.1 |
| 2 | 13.0 | V | 90.1 | 99.4 | 0.6 | — |
| 2 | 13.0 | R | 9.9 | 94.9 | 4.8 | 0.3 |

EXAMPLE 2

To show the effectiveness of evaporation for relatively impure crude ester compositions, an ester composition was prepared comprising about 4% wt monomethyl ester of FDCA, and more than 2800 ppmw impurities.

The wiped film evaporator was operated at different feed rates to obtain different ratios of vapor and residue fractions. The total duration of each test lasted 5 minutes. The evaporator was operated at a pressure of about 14-15 mbar and at a temperature of about 157° C. The temperature of the solid crude product composition that was fed into the evaporator was 153 to 157° C. The hot product composition was divided in a distillate vapor and a residue. The vapor was recovered at a temperature of 148 to 150° C., whereas the residue was discharged from the wiped film evaporator at a temperature of 145 to 146° C. The vapor was condensed to yield purified dimethyl-2,5-furandicarboxylate in a condenser located downstream of the evaporator and operating at a temperature of 120° C.

The vapors and the residues were analyzed. The analytical results of the composition of the vapors and the residues are shown in Table 2 below. The Table shows the Experiment No., the feed rate of the composition in the evaporator (F), the fraction of the vapor (V) and residue (R), respectively, based on the solid crude product composition, and the content of the FDCA-DME, FDCA-ME and the impurities in the resulting vapor and residue. The percentages are based on the vapor and residue fractions, respectively.

TABLE 2

| Exp. | F, kg/h | V/R | Fraction, % wt | FDCA-DME, % wt | FDCA-ME, % wt | Impurities, % wt |
|---|---|---|---|---|---|---|
| 3 | 8.8 | V | 34.9 | 99.1 | 0.9 | <0.01 |
| 3 | 8.8 | R | 65.1 | 92.0 | 7.5 | 0.5 |
| 4 | 4.1 | V | 67.0 | 98.9 | 1.1 | <0.01 |
| 4 | 4.1 | R | 33.0 | 89.4 | 9.8 | 0.8 |

The above experiments show that evaporation can effectively be used to remove coloration causing compounds from the solid crude product compositions. This can even effectively be done when the product composition contains a significant amount of impurities.

EXAMPLE 3

To show the effectiveness of the evaporation to improve the color properties of the resulting ester composition the UV absorbance was determined for three fractions. The first fraction was the product composition that was subjected to evaporation in Example 1. The second fraction was the distillate fraction obtained in Experiment No. 2. The third fraction was the fraction obtained after recrystallization of the solid crude product composition that was used in the evaporation tests of Example 1.

The absorbance solutions were prepared as follows: 30 mg of the sample were added to 1.0 mL of DMSO (dimethyl sulfoxide). The absorbance was measured at a wavelength of 400 nm.

The third fraction was prepared by dissolving a portion of the solid crude product composition in methanol in a solids to methanol weight ratio of 0.219. The solids were dissolved under reflux. The solution was subsequently cooled to 20° C. and a precipitate was formed. The precipitate was filtered off and dried. The resulting product was subjected to an absorbance measurement.

The results of the absorbance measurements are shown in Table 3.

TABLE 3

| Fraction | Absorbance, (30 mg/ml), $\lambda$ = 400 nm |
|---|---|
| 1 | 0.008 |
| 2 | 0.003 |
| 3 | 0.006 |

The absorbance results show that the fraction obtained after evaporation was the most transparent. As shown by the absorbance of fraction 3, recrystallization alone does not remove color causing compounds to a sufficient degree.

The invention claimed is:

1. A process for the preparation of the dialkyl esters of 2,5-furandicarboxylic acid which process comprises:
   contacting an acid starting composition comprising 2,5-furandicarboxylic acid with an excess of alkanol to form an esterification product comprising the dialkyl ester of 2,5-furan dicarboxylic acid, water and unreacted alkanol;
   separating at least part of the unreacted alkanol and water from the esterification product to yield a solid crude product composition comprising the dialkyl ester of 2,5-furandicarboxylic acid; and
   subjecting at least part of the solid crude product composition to an evaporation step, wherein the dialkyl ester of 2,5-furandicarboxylic acid is evaporated and subsequently condensed to yield purified dialkyl ester of 2,5-furandicarboxylic acid,
   wherein the solid crude product composition comprising the dialkyl ester of 2,5-furandicarboxylic acid is pre-purified in a concentration zone before being subjected to the evaporation step; and
   wherein the evaporation step is conducted in one or more of the equipment selected from a stirrer evaporator, rising film evaporator, circulation evaporator, falling film evaporator and wiped film evaporator.

2. The process according to claim 1, wherein the evaporation is carried out at a temperature in the range of 120 to 250° C.

3. The process according to claim 1, wherein the evaporation is carried out at a pressure below 100 mbar.

4. The process according to claim 1, wherein the contact of 2,5-furandicarboxylic acid with an excess of alkanol is conducted at a temperature of 150 to 300° C., and a pressure of 5 to 25 bar.

5. The process according to claim 1, wherein the contact of 2,5-furandicarboxylic acid with an excess of alkanol is conducted at a contact time of 0.1 to 3 hr.

6. The process according to claim 1, wherein the alkanol comprises 1 to 4 carbon atoms.

7. The process according to claim 1, wherein the 2,5-furandicarboxylic acid and alkanol are contacted in the absence of an esterification catalyst.

8. The process according to claim 1, wherein the 2,5-furandicarboxylic acid and alkanol are contacted in an esterification zone from which alkanol is continuously withdrawn.

9. The process according to claim 1, wherein unreacted alkanol from the esterification product is removed by means of distillation, flash distillation or evaporation.

10. The process according to claim 1, wherein the solid crude product composition is subjected to one or more of the treatments selected from washing, crystallization, re-crystallization and melt crystallization.

11. The process according to claim 1, wherein the solid crude product composition comprising the dialkyl ester of 2,5-furandicarboxylic acid is washed in a washing zone to yield washed composition comprising the dialkyl ester of 2,5-furan dicarboxylic acid, and the washed composition is crystallized in a crystallization zone to yield crystallized composition that is being subjected to the evaporation step.

12. The process according to claim 1, which is carried out at as a continuous process.

13. An ester composition comprising dialkyl ester of 2,5-furandicarboxylic acid wherein the composition comprises 99 to 99.9% wt of dialkyl ester of 2,5-furandicarboxylic acid and 1 to 0.1% wt of monoalkyl ester of 2,5-furandicarboxylic acid, the percentages being based on the composition, and which composition has a color of at most 0.005, as measured by absorbance of a 30 mg/L solution in DMSO at a wavelength of 400 nm.

14. The process according to claim 6, wherein the alkanol is methanol.

* * * * *